(12) United States Patent
Bihlmaier

(10) Patent No.: US 8,936,581 B2
(45) Date of Patent: Jan. 20, 2015

(54) CATHETER HAVING A SPIRAL SLIT

(75) Inventor: Bryan Fred Bihlmaier, Provo, UT (US)

(73) Assignee: Becton, Dickinson and Company, Franklin Lakes, NJ (US)

( * ) Notice: Subject to any disclaimer, the term of this patent is extended or adjusted under 35 U.S.C. 154(b) by 496 days.

(21) Appl. No.: 13/053,495

(22) Filed: Mar. 22, 2011

(65) Prior Publication Data
US 2012/0245562 A1 Sep. 27, 2012

(51) Int. Cl.
*A61M 5/00* (2006.01)
*A61M 25/00* (2006.01)
*A61M 5/14* (2006.01)

(52) U.S. Cl.
CPC ......... *A61M 25/007* (2013.01); *A61M 25/0074* (2013.01); *A61M 5/14* (2013.01); *A61M 25/0068* (2013.01); *A61M 2025/0073* (2013.01)
USPC .......................................... 604/264; 604/523

(58) Field of Classification Search
USPC .................................. 604/264, 523
See application file for complete search history.

(56) References Cited

U.S. PATENT DOCUMENTS

| | | | |
|---|---|---|---|
| 4,173,981 A * | 11/1979 | Mortensen | 604/8 |
| 4,623,327 A * | 11/1986 | Mahurkar | 604/6.16 |
| 4,936,826 A | 6/1990 | Amarasinghe | |
| 5,085,635 A | 2/1992 | Cragg | |
| 5,536,261 A | 7/1996 | Stevens | |
| 5,616,137 A | 4/1997 | Lindsay | |
| 5,857,464 A | 1/1999 | Desai | |
| 6,052,612 A | 4/2000 | Desai | |
| 6,129,700 A | 10/2000 | Fitz | |
| 6,293,958 B1 | 9/2001 | Berry et al. | |
| 6,669,679 B1 | 12/2003 | Savage et al. | |
| 7,108,674 B2 | 9/2006 | Quinn | |
| 2009/0287186 A1 * | 11/2009 | Adams et al. | 604/523 |
| 2010/0280316 A1 | 11/2010 | Dietz et al. | |
| 2012/0078226 A1 * | 3/2012 | Latere Dwan'isa et al. | 604/506 |

FOREIGN PATENT DOCUMENTS

| | | |
|---|---|---|
| DE | 30 33 459 A1 | 4/1982 |
| EP | 0 348 136 A2 | 12/1989 |
| GB | 955490 | 4/1964 |
| GB | 2 043 457 A | 10/1980 |
| JP | 2000-167061 A | 6/2000 |
| WO | WO 01/91830 A1 | 12/2001 |

OTHER PUBLICATIONS

"AJR: Modified Catheter Can Reduce Contrast Material Injuries," Health Imaging.com, Clinical Studies, http://www.healthimaging.com/index.php?view=article&id=18807%3Aajr-modified-cath . . . , 1 page, Oct. 21, 2009.
Weber, Paul W. et al., "AJR: Modifying Peripheral IV Catheters with Side Holes and Side Slits Results in Favorable CHanges in Fluid Dynamic Properties During the Injection of Iodinated Contrast Material," pp. 970-977, AJR:193, Oct. 2009.

* cited by examiner

*Primary Examiner* — Emily Schmidt
(74) *Attorney, Agent, or Firm* — Jeanne Lukasavage; Craig Metcalf; Kirton McConkie

(57) ABSTRACT

A catheter having a catheter body with a lumen and a distal lumen opening. The catheter's lumen extends through the catheter body along a longitudinal axis of the catheter body. A spiral slit is formed through a wall of the catheter body.

20 Claims, 9 Drawing Sheets

CATHETER HAVING A SPIRAL SLIT

BACKGROUND

Vascular access devices are used for communicating fluid with the anatomy of a patient. For example, vascular access devices, such as catheters, are commonly used for infusing fluid, such as saline solution, various medicaments, and/or total parenteral nutrition, into a patient, withdrawing blood from a patient, and/or monitoring various parameters of the patient's vascular system.

A variety of clinical circumstances, including massive trauma, major surgical procedures, massive burns, and certain disease states, such as pancreatitis and diabetic ketoacidosis, can produce profound circulatory volume depletion. This depletion can be caused from actual blood loss or from internal fluid imbalance. In these clinical settings, it may be necessary to infuse blood and/or other fluid rapidly into a patient to avert serious consequences.

Additionally, the ability to inject large quantities of fluid in a rapid manner may be desirable for certain other medical and diagnostic procedures. For example, some diagnostic imaging procedures utilize contrast media enhancement to improve lesion conspicuity in an effort to increase early diagnostic yield. These procedures necessitate that viscous contrast media be injected by a specialized "power injector" pump intravenously at very high flow rates, which establishes a contrast bolus or small plug of contrast media in the bloodstream of the patient which results in enhanced image quality.

Power injection procedures generate high pressures within the infusion system, thereby requiring some specialized vascular access devices, extension sets, media transfer sets, pump syringes, and bulk or pre-filled contrast media syringes. As the concentration (and thereby viscosity) and infusion rate of the contrast media are increased, bolus density also increases resulting in better image quality via computed tomography (CT) attenuation. Therefore, a current trend in healthcare is to increase the bolus density of the contrast media by increasing both the concentration of the contrast media and the rate at which the media is infused into the patient, all of which ultimately drives system pressure requirements higher.

Intravenous infusion rates may be defined as either routine, generally up to 999 cubic centimeters per hour (cc/hr), or rapid, generally between about 999 cc/hr and 90,000 cc/hr (1.5 liters per minute) or higher. For some diagnostic procedures utilizing viscous contrast media, an injection rate of about 1 to 10 ml/second is needed to ensure sufficient bolus concentration. Power injections of viscous media at this injection rate produce significant back pressure within the infusion system that commonly results in a failure of the infusion system components.

Traditionally, rapid infusion therapy entails the use of an intravenous catheter attached to a peristaltic pump and a fluid source. A patient is infused as a tip portion of the catheter is inserted into the vasculature of a patient and the pump forces a fluid through the catheter and into the patient's vein. Current rapid infusion therapies utilize a catheter and catheter tip with geometries identical to those used with traditional, routine infusion rates. These geometries may include a tapering catheter tip such that the fluid is accelerated as the fluid moves through the catheter tip and exits into a patient's vasculature. This acceleration of the infused fluid is undesirable for several reasons.

For example, the tapered catheter results in a greater backpressure for the remainder of the catheter assembly. This effect is undesirable due to the limitations of the pumping capacity of the infusion pump as well as the limited structural integrity of the components and subcomponents of the infusion system. For example, if the backpressure becomes too great, the pump's efficiency may decrease and certain seals or connections within the infusion system may fail. Additionally, the fluid acceleration in the catheter tip results in a recoil force that may cause the catheter tip to shift within the patient's vein thereby displacing the catheter and/or damaging the patient's vein and/or injection site. Fluid acceleration also increases the jet velocity of the infusant at the tip of the catheter. In some procedures, the fluid jet may pierce the patient's vein wall thereby leading to extravasation or infiltration. Not only is this uncomfortable and painful to the patient, but infiltration may also prevent the patient from receiving the needed therapy.

SUMMARY

The systems and methods of the present disclosure have been developed in response to problems and needs in the art that have not yet been fully resolved by currently available infusion systems and methods. Thus, these systems, components, and methods are developed to provide for safer and more efficient rapid infusion procedures.

One aspect of the invention provides an improved vascular access device for use in combination with a vascular infusion system capable of rapidly delivering an infusant to the vascular system of a patient. Some embodiments of the invention can be configured as follows. The vascular access device can include an intravenous catheter configured to access the vascular system of a patient. The intravenous catheter can have a lumen extending therethrough along a longitudinal axis to a distal lumen opening. The tip portion can comprise a tapered portion, wherein the outer and inner surface of the tip taper towards the distal end of the catheter. The tapered portion of the intravenous catheter can be modified to include a spiral slit formed though a wall of the catheter body.

In another aspect of the invention, a catheter has a catheter body, which has a lumen and a distal lumen opening. The lumen can extend through the catheter body along a longitudinal axis of the catheter body to the distal lumen opening. The catheter can also have a spiral slit formed through a distal tapered portion of the catheter body.

In yet another aspect of the invention, a peripheral catheter includes a catheter body that has a lumen and a distal lumen opening. The lumen extends through the catheter body along a longitudinal axis of the catheter body. The catheter body has a truncated length sufficient to access a peripheral vein of a patient, and the catheter body is sized smaller than or equal to a fourteen gauge catheter. A spiral slit is formed through a distal, tapered portion of the catheter body. The spiral slit extends proximately less than or equal to approximately one-quarter inch from the distal tip of the catheter body. A plane located on and extending along the longitudinal axis of the catheter body intersects the catheter body at an angle between 30° to 60° degrees to the spiral slit.

BRIEF DESCRIPTION OF THE SEVERAL VIEWS OF THE DRAWINGS

In order that the manner in which the above-recited and other features and advantages of the invention are obtained will be readily understood, a more particular description of the invention briefly described above will be rendered by reference to specific embodiments thereof which are illustrated in the appended drawings. These drawings depict only

DETAILED DESCRIPTION OF THE INVENTION

Embodiments of the present invention will be best understood by reference to the drawings, wherein like reference numbers indicate identical or functionally similar elements. It will be readily understood that the components of the present invention, as generally described and illustrated in the figures herein, could be arranged and designed in a wide variety of different configurations. Thus, the following more detailed description, as represented in the figures, is not intended to limit the scope of the invention as claimed, but is merely representative of presently preferred embodiments of the invention.

Figure 1:
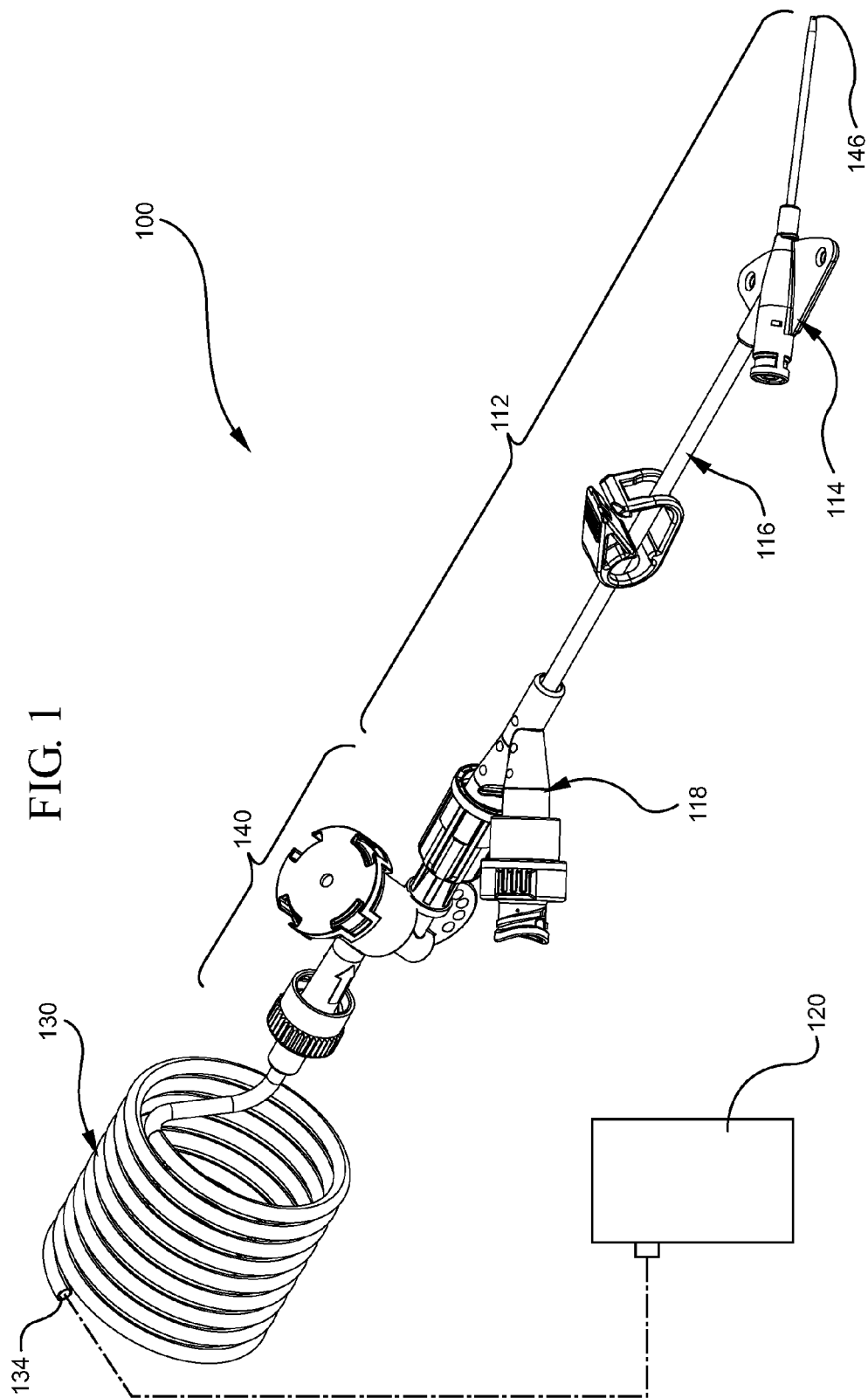
FIG. 1 is a perspective view of an infusion system in accordance with a representative embodiment of the present invention.

The systems and methods of the present invention are generally designed for use in combination with a vascular infusion system capable of rapidly delivering an infusant to the vascular system of a patient. Referring now to FIG. 1, a vascular infusion system 100 is shown, in accordance with a representative embodiment of the present invention. Infusion systems of this type are commonly configured to operate at internal pressures up to 2000 psi. Many systems operate in the range of 75 to 2000 psi, while specific devices of this type operate at 100, 200, and 300 psi. The vascular infusion system 100 comprises a vascular access device 112 coupled to an injector pump 120 via a coiled extension set 130. In some embodiments, the infusion system 100 further comprises a safety device 140 positioned between the vascular access device 112 and the injector pump 120. In some embodiments, a safety device 140 is provided to automatically occlude the fluid path of the infusion system 100, thereby preventing excessive pressure buildup in downstream infusion components.

An injector pump 120 generally comprises a fluid pumping apparatus configured to rapidly deliver an infusant, such as blood, medicaments, and CT scan contrast agents to a patient's vascular system. Desirable infusants may also include various fluids often of high viscosity as required for medical and diagnostic procedures. In some embodiments, the injector pump 120 comprises a power injector capable of delivering an infusant to a patient at flow rates from about 10 mL/hour up to about 1200 mL/minute. In some embodiments, a high infusion flow rate is desirable for medical procedures which require enhanced bolus density of an infusant in a patient's vascular system. For example, a trend in diagnostic imaging procedures is to utilize contrast media enhancement, which requires more viscous contrast media to be pushed into a patient at a higher flow rate, thereby resulting in increased image quality. Thus, in some embodiments an injector pump 120 and a vascular access device 112 are selected to compatibly achieve a desired infusion flow rate.

A coiled extension set 130 generally comprises flexible or semi-flexible polymer tubing configured to deliver an infusant from the injector pump 120 to the vascular access device 112. The extension set 130 includes a first coupler 132 for connecting the extension set 130 to a downstream device 112 or 140. The extension set 130 also includes a second coupler 134 for connecting the extension set 130 to the injector pump 120. A coiled configuration of the extension set 130 generally prevents undesirable kinking or occlusion of the set 130 during infusion procedures. However, one of skill in the art will appreciate that the extension set 130 may include any configuration capable of efficiently delivering an infusant from an injector pump 120 to the patient via a vascular access device 112. In some embodiments, the extension set 130 is coupled between a syringe and a vascular access device whereby an infusant is manually injected into a patient. In other embodiments, the infusion system comprises only a syringe and a vascular access device, in accordance with the present invention.

The vascular access device 112 generally comprises a peripheral intravenous catheter 114. A peripheral intravenous catheter 114 in accordance with the present invention generally comprises a short or truncated catheter (usually 13 mm to 52 mm) that is inserted into a small peripheral vein. Such catheters generally comprise a diameter of approximately a 14 gauge catheter or smaller. Peripheral intravenous catheters 114 are typically designed for temporary placement. The short length of the catheter 114 facilitates convenient placement of the catheter but makes them prone to premature dislodging from the vein due to movement of the patient and/or recoil forces experienced during infusion procedures. Furthermore, unlike midline or central peripheral catheters, peripheral intravenous catheters 114 in accordance with the present invention comprise a tapered catheter tip 146 to accommodate use with an introducer needle (not shown) designed to aid in insertion of the catheter 114.

The tapered outer surface of the catheter tip 146 can provide a smooth transition between the narrow diameter of the catheter tip opening and the larger diameter of the catheter tubing. Thus, as the tip 146 of the catheter 114 is introduced into the vein of a patient, the tapered outer surface 146 facilitates easy insertion of the catheter 114 through the access hole. The tapered inner surface is generally provided to tightly contact the outer surface of an introducer needle housed within the lumen of the catheter. The introducer needle is provided to create an opening into the vein of patient through which the catheter tip is inserted. The tapered inner surface ensures a tight seal between the inner surface of the catheter and the outer surface of the needle. Following placement of the catheter, the introducer needle is removed.

An introducer needle is typically inserted through the catheter 114 such that a tip of the needle extends beyond the tapered tip 146. The tapered geometry of the tapered tip 146 conforms tightly to the outer surface of the introducer needle. Both the outer surface and the inner surface of the tip 146 are tapered towards the distal end of the catheter 114. The outer surface of the tip 146 is tapered to provide a smooth transition from the smaller profile of the introducer needle to the larger profile of the catheter outer diameter. Insertion of the introducer needle into the vein of the patient provides an opening into the vein through which the tapered tip 146 of the catheter 114 is inserted. The tapered outer surface of the tip 146 enables easy insertion of the catheter 114 into the opening. Once the peripheral intravenous catheter 114 is inserted into the vein of the patient, the introducer needle (not shown) is removed from the lumen of the catheter 114 to permit infusion via the catheter 114.

The tapered inner surface of the tip 146 provides a secure seal between the inner surface of the catheter tip 146 and the outer surface of the introducer needle (not shown). Additionally, the tapered inner surface of the tip 146 causes an acceleration of infusant within the lumen of the catheter as the infusant nears and flows through the catheter tip 146. Specifics regarding the geometries of the tapered inner surface of the tip 146 are provided in connection with FIGS. 3 and 4 below. Following an infusion procedure, the peripheral intravenous catheter 114 is simply removed from vein and discarded.

A desired infusant is typically delivered to the catheter 114 via a section of intravenous tubing 116 coupled to the catheter 114. In some embodiments, a y-adapter 118 is coupled to an end of the tubing 116 opposite the catheter 114, enabling the vascular access device 112 to be coupled to the remainder of the vascular infusion system 100. One of skill in the art will appreciate the possible variations and specific features of available vascular access devices 112, as are commonly used in the medical and research professions. For example, in some embodiments a catheter 114 in accordance with the present invention may include additional access sites, clamps, parallel intravenous lines, valves, couplers, introducer needles, coatings, and/or materials as desired to fit a specific application.

Figure 2:
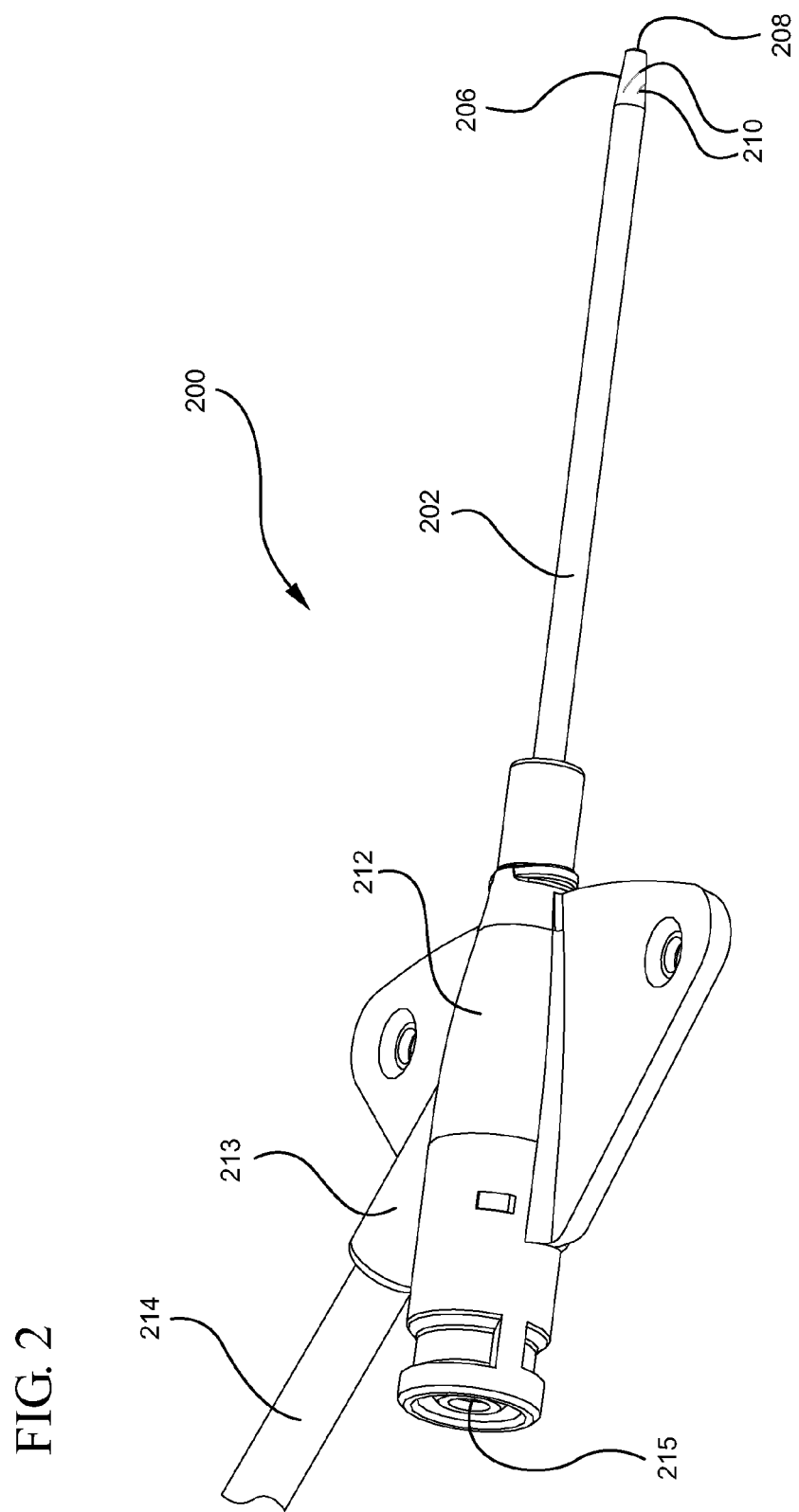
FIG. 2 is a detailed perspective view of a catheter with slits of its distal end in accordance with a representative embodiment of the present invention.

Referring now to FIG. 2, a catheter 200 is shown in accordance with a representative embodiment of the present invention. Catheter 200 generally comprises a catheter adapter 212 configured to house a tubular body member 202. Catheter adapter 212 further includes an inlet port 213 that is coupled to a section of intravenous tubing 214. The section of intravenous tubing 214 is further coupled to upstream infusion components, as shown and described in connection with FIG. 1, above.

The catheter adapter 212 facilitates delivery of an infusant within the intravenous tubing 214 to a patient via the tubular body member 202. An inner lumen of the catheter adapter 212 is in fluid communication with both an inner lumen of the intravenous tubing 214 and an inner lumen of the tubular body member 202. In some embodiments, catheter adapter 212 further comprises an access port 215. The access port 215 is generally provided to permit direct access to the inner lumen of the catheter adapter 212. In some embodiments, the access port 215 is accessed via a needle and a syringe to deliver an infusant to a patient via the tubular body member 202. In other embodiments, an introducer needle or guide wire is inserted into the access port 215 and advanced through the inner lumen of the tubular body member 202. In some embodiments, a tip portion of the introducer needle or guide wire (not shown) extends beyond a tip portion 206 of the tubular body member 202. As such, the tip portion of the introducer needle or guide wire may provide an opening into the vascular system of a patient into which the tubular body member 202 is inserted. Following placement of the tubular body member 202 into the vein of the patient, the introducer needle or guide wire is removed from the access port 215 thereby establishing fluid communication between the tubular body member 202, the catheter adapter 212 and the intravenous tubing 214.

In some embodiments, the tubular body member 202 is an intravenous catheter (or catheter body). The intravenous catheter 202 generally comprises a flexible or semi-flexible biocompatible material, as commonly used in the art. In some embodiments, the intravenous catheter 202 comprises a polymer material, such as polypropylene, polystyrene, polyvinylchloride, polytetrafluoroethylene, and the like. In other embodiments, the intravenous catheter 202 comprises a metallic material, such as surgical steel, titanium, cobalt steel, and the like.

The tubular body member 202 may comprise any length, where the length is selected based on the intended application of the catheter 200. For some applications, the tubular body member 202 is inserted into a peripheral vein of the patient. In other applications, the tubular body member 202 is inserted into a central vein of the patient. For rapid infusion applications, the tip portion 206 of the tubular body member 202 is modified to include a plurality of slits 210. The slits 210 are generally provided to divert fluid from the main channel of flow through the inner lumen of the tubular body member 202. As such, the slits 210 effectually slow the jet of infusant which issues from the catheter tip 206 during rapid infusion procedures. Additionally, the plurality of slits 210 increase the accumulative area of the catheter tip opening 208 to relieve the overall pressure in the vascular infusion system 100.

Slits 210 generally include long narrow cuts or openings formed completely through a wall of the catheter body 202. In some embodiments, the slits 210 are long relative to their width, and are directed at an angle to the longitudinal axis of the catheter, forming a helical shape along a length of the distal end of the catheter. In some configurations, only a single slit 210 is formed on the distal end of the catheter. In other configurations, two or three slits 210 are formed thereon. Still in other embodiments, four, five, or six slits 210 are formed thereon. In some embodiments, more than six slits 210 are formed thereon.

One or more slits 210 can be disposed on the portion of the catheter body 202 that is inserted complete into the vasculature of a patient. In some embodiments, this is the distal portion of the catheter body 202. The length of this extension can thus depend on the length of the catheter body 202 and the distance between the patient's skin and the patient's vasculature. In some embodiments, one or more slits 210 are disposed only on the ¼-inch of the catheter body 202. In other words, the one or more slits 210 extend proximally from the distal end of the catheter body 202 a distance of a ¼-inch. In other instances, slits 210 are disposed on the distal 1/32-inch, 1/16-inch, ⅛-inch, ½-inch, ¾-inch, 1-inch 2-inches, or 3-inches.

In some embodiments, during high pressure fluid infusions, fluid pressure within the catheter body 202 creates axial tension on the catheter tip, which can spread open the slit surfaces 210a and 210b of the slit 210 to create a slit opening 240 through which fluid can escape. In some instances, a slit 210 opens, creating expanded slit openings 240 as the slit surfaces 210a and 210b are drawn apart. In some configurations, as a slit 210 opens the distal catheter tip naturally rotates to accommodate the movement of the slit opening 240. This opening action can occur whether one or several slits 210 are formed through the catheter body 202. Examples of such openings 240 are described below and illustrated in the figures.

Additionally, slits 210 can benefit the catheter system by providing relatively high degrees of compressive strength to the catheter body 202 compared to other types of cutouts that might otherwise be formed on the catheter's distal tip. For example, during catheter insertions, as the distal end of the catheter body 202 is forced against a patient's skin, the patient's skin can apply an axial compressive force 218 against the catheter body 202. In some instances, this force can cause some embodiments of catheter holes on the distal tip of catheter to buckle under this compressive force 218. In contrast, a slit 210 can resist this high compressive force 218 as the slit's opposing slit surfaces 210a and 210b compress together while remaining closed. As such, the slit 210 can be inserted through the skin and tissue of a patient without buckling, snagging, or shearing the skin or tissue. These advantages can simplify the insertion procedure, facilitate the job of medical clinicians, and ease pain and damage to the patient.

Slits 210 formed on a catheter tip can provide advantages to the catheter system and the insertion and infusion process. For example, one or more slits (e.g. spiral slits) 210 formed on the distal portion of the catheter body 202 can reduce the velocity of a fluid jet exiting the catheter tip, thus reducing the jet's impact and potential for damage to vein walls. Additionally, one or more slits 210 on a distal portion of the catheter tip portion can reduce pressure loss that may be otherwise caused by the presence of a tapered end on a catheter tip as fluid flows through the slits 210 within the tapered tip. Furthermore, one or more slits 210 on a distal portion of the catheter can reduce the overall system pressure and permit higher injection rates for pressure-limited power injector systems.

Figure 3:
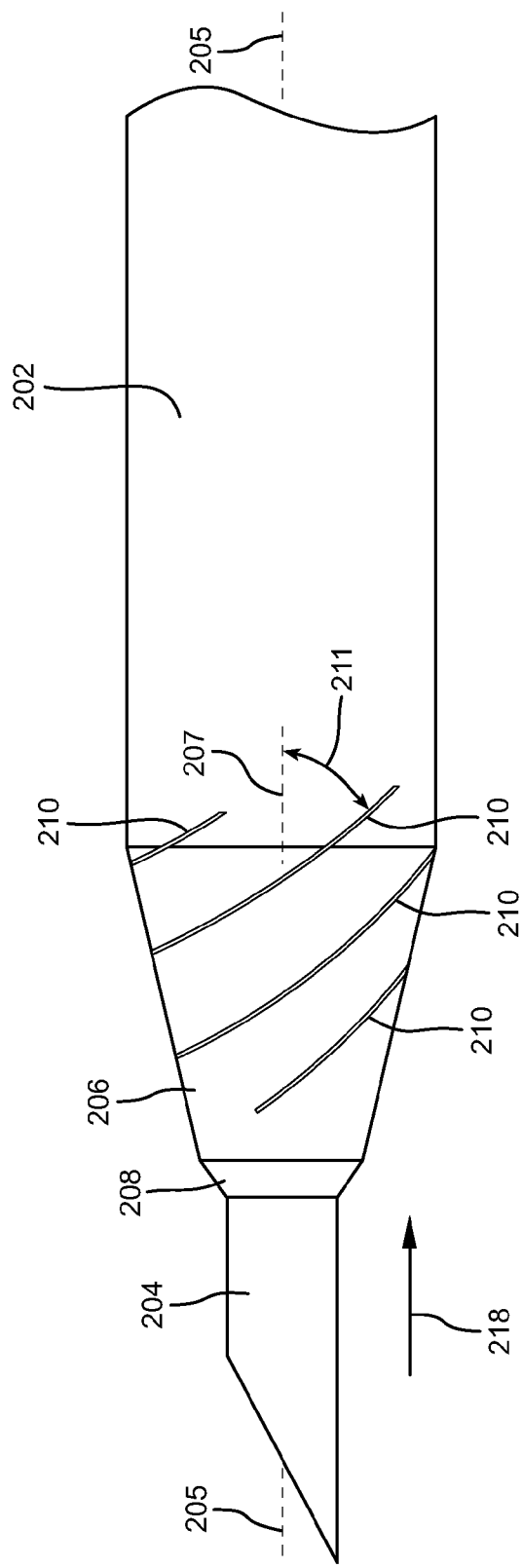
FIG. 3 is a perspective view of a catheter tip having slits and an introducer needle extending therethrough in accordance with a representative embodiment of the present invention.

An example of catheter body 202 having four representative slits 210 is shown in FIG. 3, according to some embodiments. As shown, the catheter body 202 includes a tapered portion 206 on its distal end portion. An introducer needle 204 is passed through the lumen 220 of the catheter body 202 and extends out the distal lumen opening 221. The distal end of the tapered portion includes a steep tapered portion 208 that can prevent skin from snagging on the catheter tip.

In some configurations, the one or more slits 210 are spiral slits, being long narrow cuts or openings that wind in a constant longitudinal direction (distally or proximally) along the catheter body 202, such as those shown in FIG. 3. Specifically, a slit 210 can be a mere cut with an insubstantial width, such that the slit's two opposing surfaces are substantially in contact along the length of the slit 210 when the catheter is unused. Alternatively, a slit 210 can be an opening with one or more defined width(s), such that the slit's two opposing surfaces are not in contact along the entire length of the slit 210 when the catheter is unused.

It can be beneficial to include more than one slit 210 on the catheter body 202. For example, the catheter body 202 depicted in FIGS. 22-23 includes four slits 210, while that of FIG. 6-8 includes two slits 210. Alternatively, the catheter bodies 202 depicted in FIGS. 24 and 28 depict only a single slit 210. Multiple slits 210 can increase the number of slit openings 240, while enabling fluid diffusing in multiple directions. Accordingly, six or more slits 210 can be formed through the catheter body walls.

To provide an effective number of slits 210 and slit configurations, the number of slits 210 can be, at least partially, dependent on the angle of inclination 211 of the slits and the length of the slits 210. The angle of inclination 211 of the slit 210 is between the direction of the slit 210 and the line of intersection 207 of a plane passing along and extending from the longitudinal axis 205 and the catheter body 202, as shown in FIG. 3. For example, a slit 210 having a 60° angle of inclination 211, if wrapped one complete time around the catheter body 202 will not provide as much space between the distal and proximal ends of the slit 210 as it would if its angle of inclination 211 were, for example 30°. Accordingly, in some embodiments, a catheter body 202 having longer slits 210 with large angles of inclination 211 may have fewer slits 210 than if the length of the slit 210 or the slit's angle of inclination 211 were decreased.

Spiral slits 210 can be formed having a various angle of inclination 211. For example, in some embodiments, the angle of inclination 211 is between 15°-75°. In other embodiments, the angle of inclination 211 is between 30°-60°. In still other embodiments, the angle of inclination 211 is between 40°-50°. These ranges are only representative. Accordingly, one or more slits 210 can be disposed at other angles of inclination 211. Additionally, two or more slits 210 on the same catheter body 202 can be formed at different angles of inclination 211.

Similarly, slits 210 can extend to varying degrees around the catheter body 202. To clarify, a slit 210 extending 360° around the catheter body 202 encompasses the catheter body 202 one full time, and a slit 210 extending 90° around the catheter body 202 encompasses only one quarter of the catheter body 202. Accordingly, in some embodiments, a slit 210 extends between 3°-720° around the catheter body 202. In other embodiments, a slit 210 extends between 10°-360° around the catheter body 202. In still other embodiments, a slit 210 extends between 30°-180° around the catheter body 202. As shown in FIG. 3, the slits 210 extend between 180°-360° around the catheter body 202. In some embodiments, two or more different slits 210 formed on the catheter body 202 extend to different degrees around the catheter body 202. Additionally, slits 210 can also have various lengths. In some embodiments, a slit 210 extends between ¹⁄₃₂-inch to 3-inches. In other embodiments, a slit 210 extends between ¹⁄₁₆-inch to-1-inch. In still other embodiments, a slit 210 extends between ⅛-inch to ¼-inch.

Figure 4:
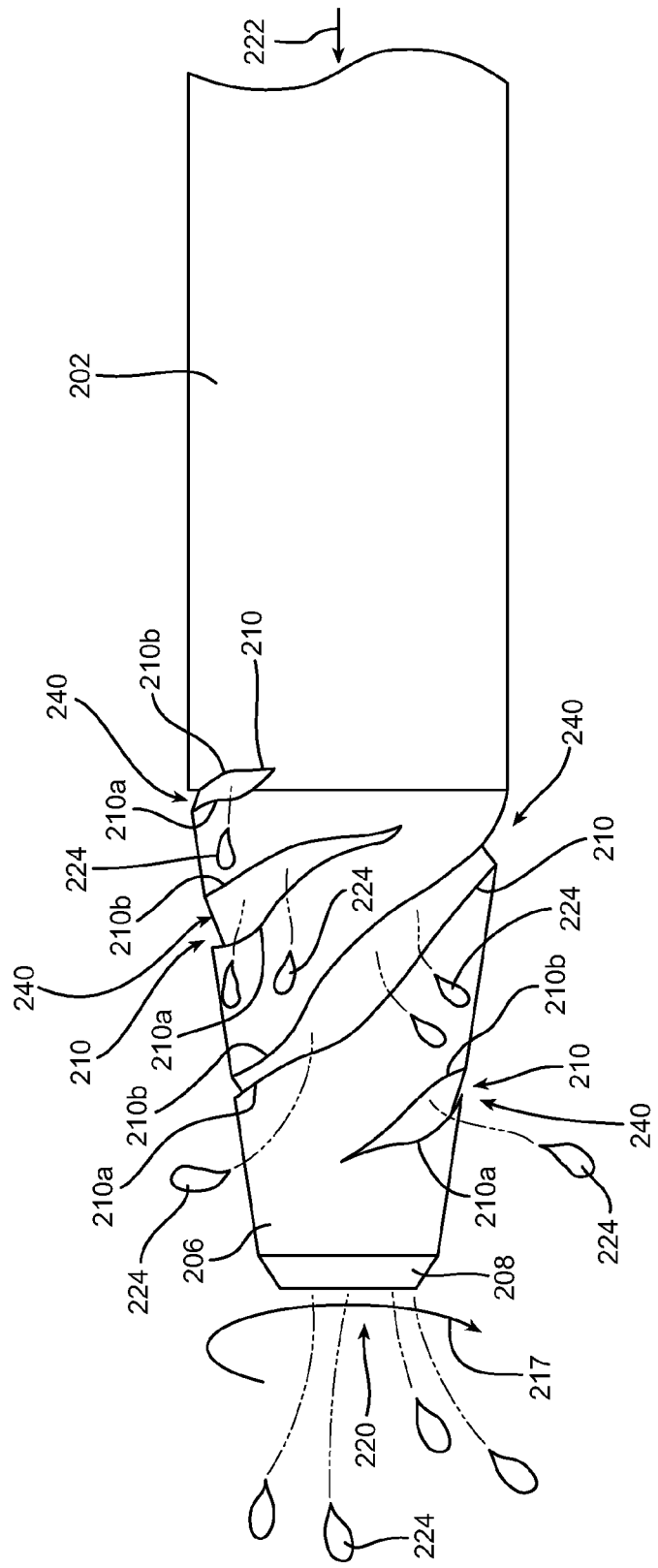
FIG. 4 is a perspective view of the catheter tip of FIG. 3, after removal of the needle and during fluid infusion in accordance with a representative embodiment of the present invention.

As mentioned, when fluid is infused through a catheter, pressure within the catheter increases placing a force 222 against the inner surfaces of the lumen 220 and opening the slits 210. FIG. 4 shows a representative embodiment of the catheter body 202 with open slits 210 and fluid 224 flowing therefrom as well as from the distal lumen opening 221. Opposing slit surfaces 210a and 210b form slit openings 240. As shown, as the slits 210 open, the distal portion of the catheter body 202 can naturally rotates about the longitudinal axis 205. As shown and explained above, in some embodiments, the slits 210 open in a manner similar to that of a tube of ready-made biscuits, allowing fluid to flow through slit openings 240 between the slit's opposing surfaces 210a and 210b.

Figure 5:
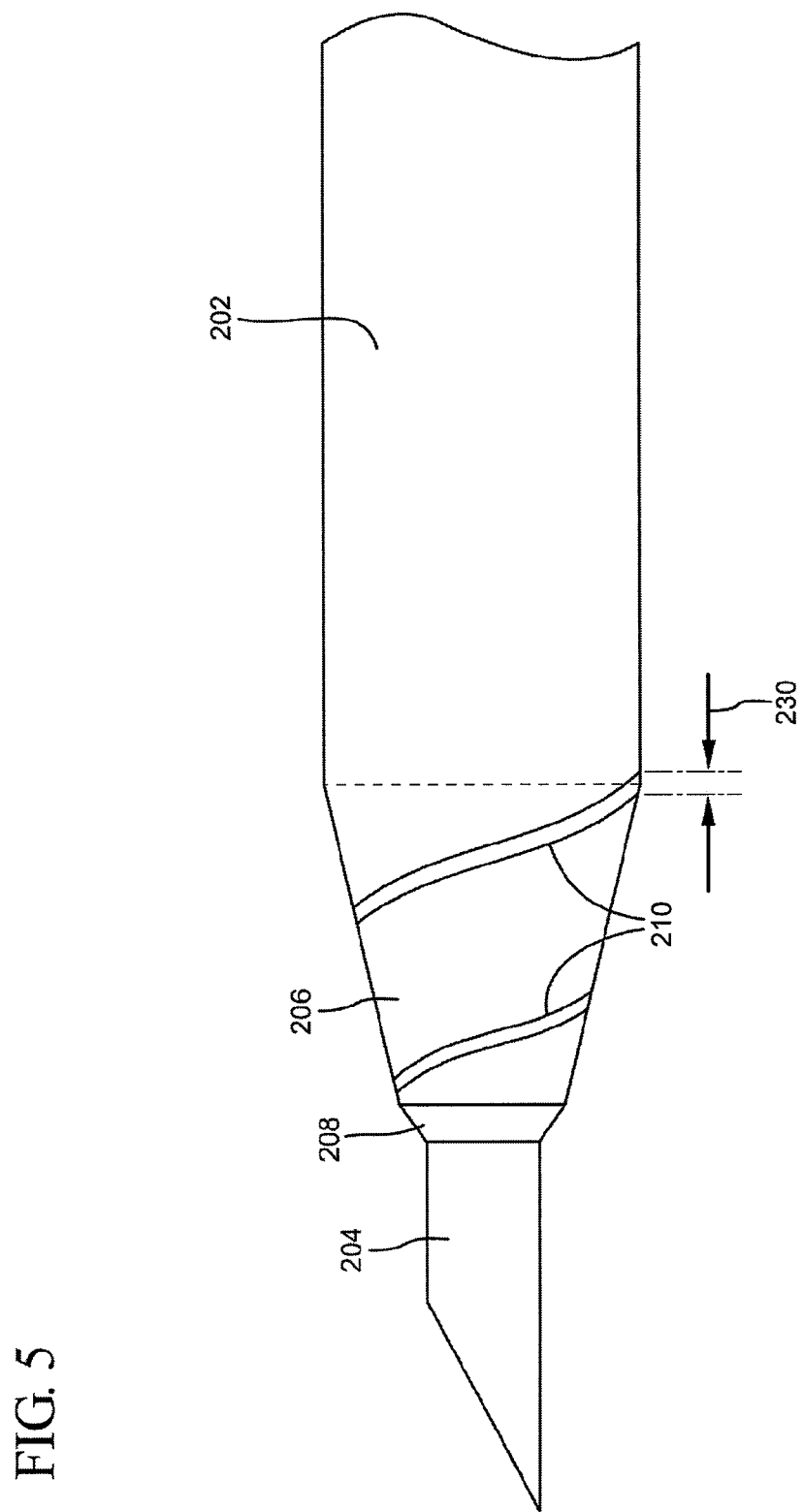
FIG. 5 is a perspective view of a catheter tip having a slit in accordance with a representative embodiment of the present invention.

Referring now to FIG. 5, which illustrates a catheter body 202 having a single slit 210 formed on a tapered portion 206 on its distal end. As shown, the slit 210 is an opening, as discussed above, having a defined width 230. In some embodiments, this defined width 230 permits the slit 210 to have a larger opening when fluid is infused through the lumen 220 of the catheter body 202. In some configurations, a slit 210 that is an opening can remain open, such that the slit's two opposing surfaces are not in contact along the entire length of the slit 210 when the catheter is unused.

Figure 7:
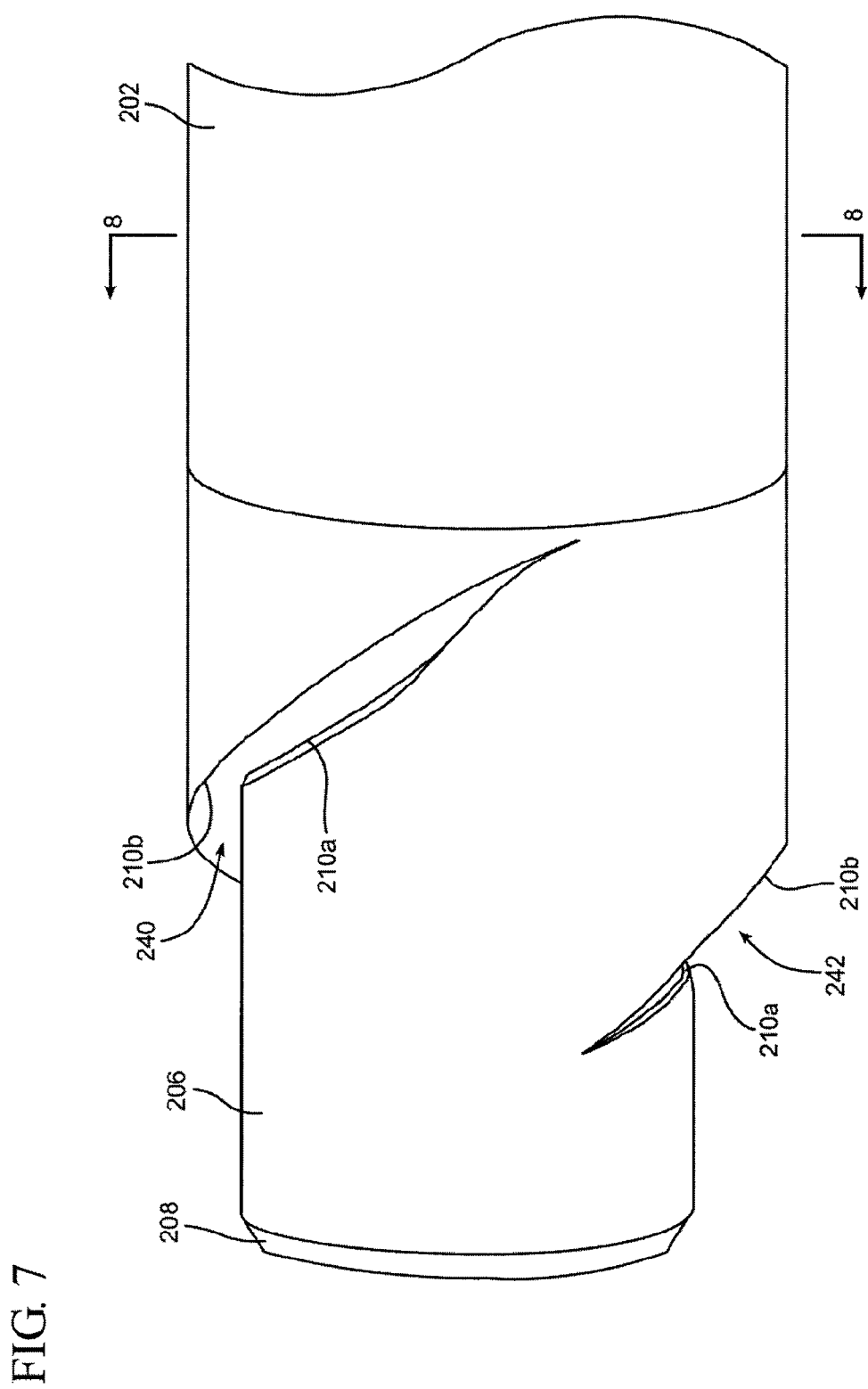
FIG. 7 is a perspective view of the catheter tip of FIG. 6 with open slits in accordance with a representative embodiment of the present invention.
Figure 8:
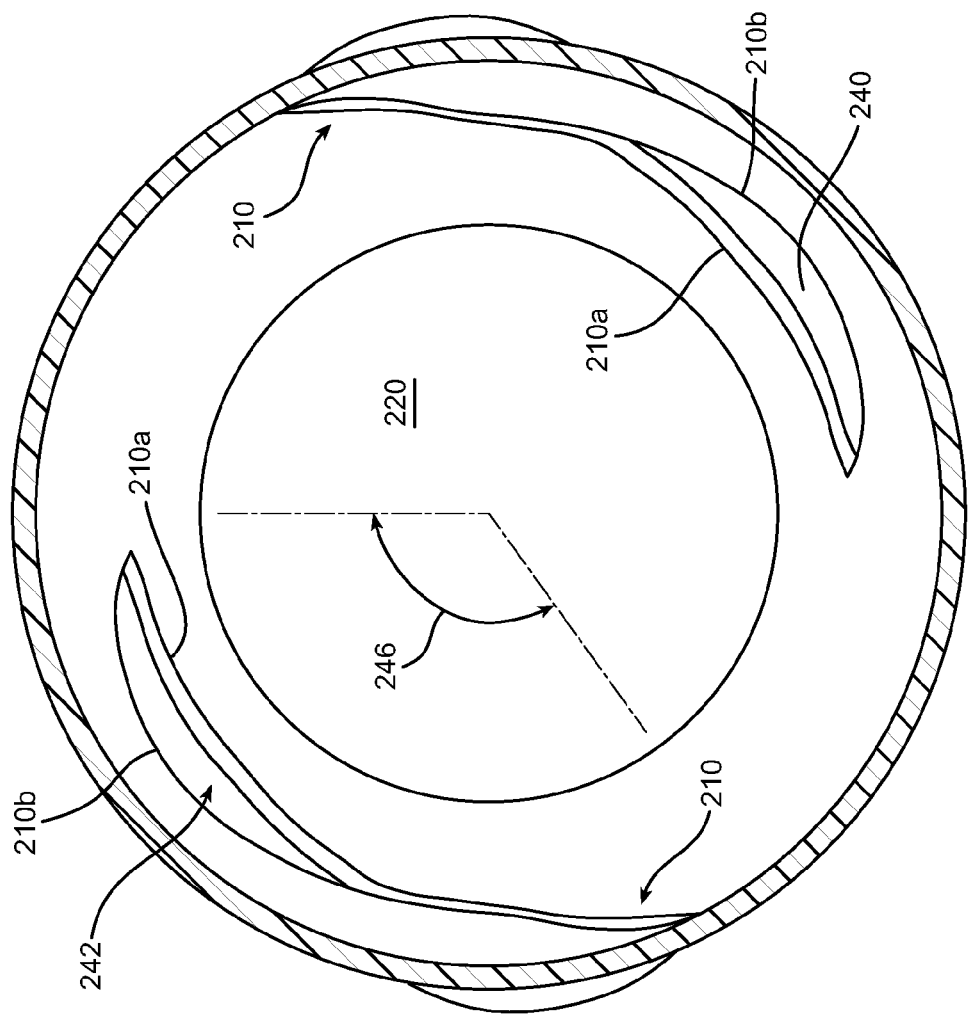
FIG. 8 is a cross-sectional view of the catheter tip of FIG. 7 taken along line 8-8 in accordance with a representative embodiment of the present invention.

Referring now to FIG. 7, which illustrates one example of a manner in which two slits 210 can open in response to fluid pressure within the lumen 220. FIG. 7 shows a catheter body 202 having two closed slits 210 in a closed position. As fluid is introduced through the catheter's lumen 220, the slits 210 open inwardly and/or outwardly, as shown in FIG. 8. As shown, the slits 210 open to form slit openings 240 that permit increased fluid to flow therethrough. Furthermore, in some instances, the shape of the slit openings 240 and 242 may create turbulence in jets of fluid exiting these openings, which can, as explained above, slow the flow of the fluid exiting the catheter.

FIG. 8 illustrates a cross sectional view of the catheter body 202 of FIG. 7, taken along line 248, which more clearly represents an example of slit openings 240. This view looks down the distal end of the catheter lumen 220. As depicted, the two slits 210 are in an open position, in which a portion of the slit openings 240 and the slit surfaces 210a and 210b are visible. FIG. 8 also shows the degree to which the slits 210 extend around the catheter body 202. As shown, one slit 210 extends around the catheter body at an angle 246 that is between 90°-180°.

Figure 6:
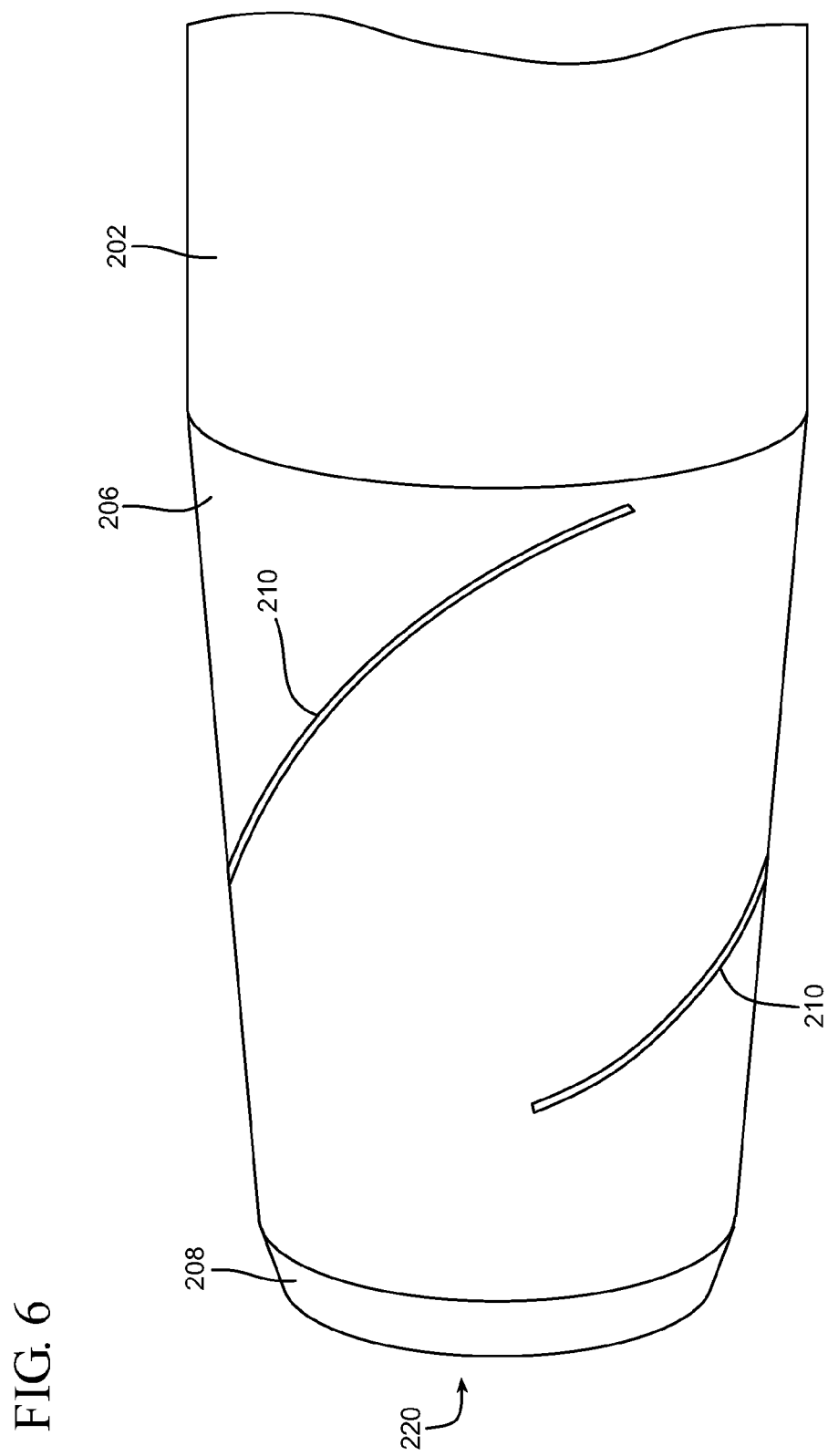
FIG. 6 is a perspective view of a catheter tip having two slits in accordance with a representative embodiment of the present invention.

In some embodiments, the ability of the slits 210 to open is enhanced by forming the slits 210 on the tapered portion 206 of the catheter body 202 since this portion may tend to have increased internal pressures. The increased pressure can facilitate slit openings 240. Accordingly, in some configurations, slits 210 are formed at least partially on a tapered portion 206 of the catheter body 202. In some instances, such as that shown in FIG. 3, the slits 210 are disposed partially on the tapered portion 206 and partially on a non-tapered portion of the catheter body 202. In other instances, one or more slits 210 are disposed either entirely on a tapered portion 206 or entirely on a non-tapered portion of the catheter body 202, as depicted in FIG. 6-8.

When disposed on a tapered portion 206 of the catheter body 202 slits 210 can reduce the adverse effects of the tapered portion 206, while preserving the tapered portion's 206 beneficial functions. As mentioned, a tapered portion 206 on a distal portion of a catheter body 202 can provide a smooth transition between the narrow diameter of the catheter tip opening and the larger diameter of the catheter body 202. However, the tapered portion 206 can also negatively affect the vascular infusion system by accelerating fluid therethrough, which can cause back pressure within the system, recoil force, broken system seals, and an increased risk of extravasation due to the increased exit velocity. Accordingly, by disposing one or more slits 210 on the tapered portion 206 fluid flows through the slit openings 240, thus minimizing increases in acceleration with its attendant effects.

Figure 9:
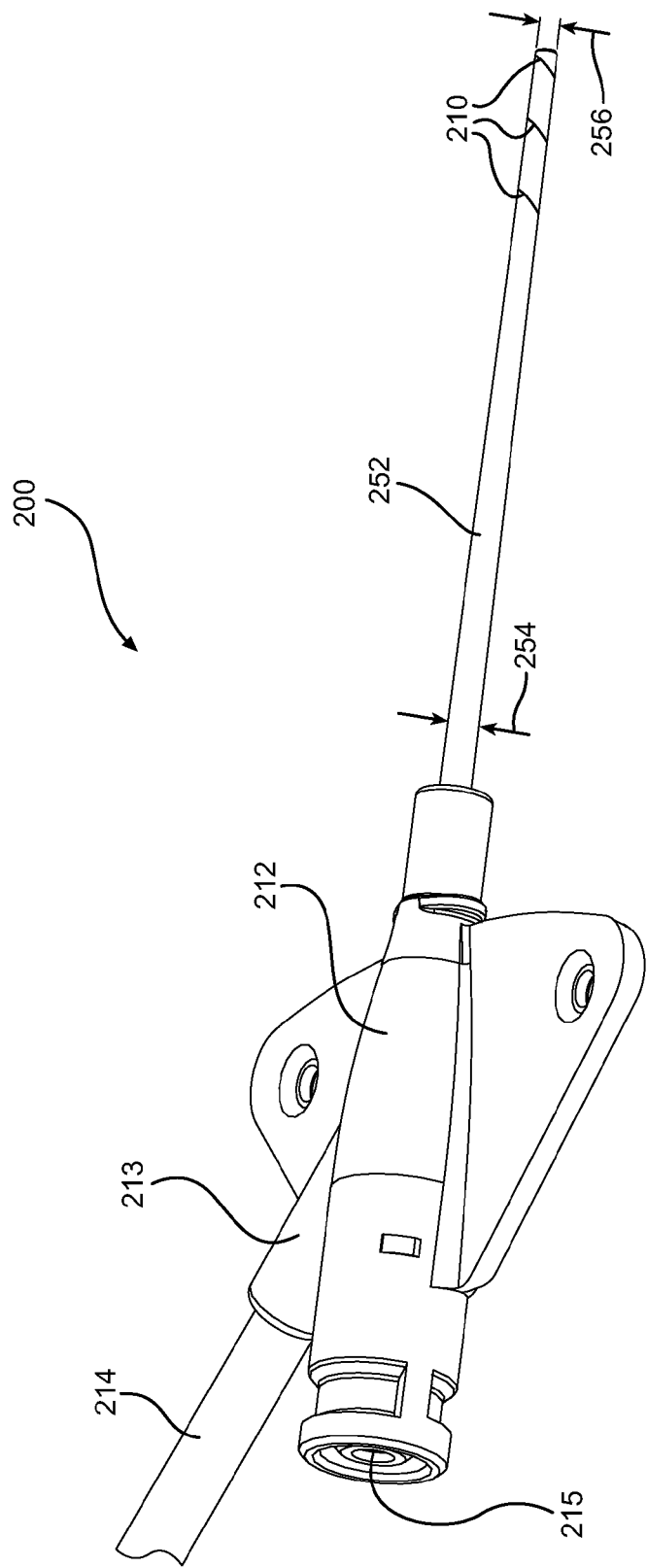
FIG. 9 is a detailed perspective view of a catheter having a tapered catheter in accordance with a representative embodiment of the present invention.

To provide for longer slit lengths and/or to provide other benefits, the tapered portion 206 can be extended to have greater lengths. For example, in some embodiments, the tapered portion 206 extended between 1/32-inch to 1/2-inch from the distal tip of the catheter. In other embodiments, the tapered portion 206 extends between 1/16-inch to 1/4-inch from the distal tip of the catheter. Alternatively, as shown in FIG. 9, the entire length of the catheter body 252 can be tapered. Accordingly, a catheter body 252 can have a constant taper along substantially its entire length, resulting in a proximal width 254 that is larger than the distal width 256. For example, the catheter can have a proximal width 254 of a fourteen gauge catheter and a distal width of a sixteen gauge catheter. Likewise, a tapered catheter body 252 can have other dimensions and sizes.

From the foregoing it will be seen that one or more slits 210, including spiral slits 210, can benefit the catheter system by providing relatively high degrees of compressive strength to the catheter body compared to other types of cutouts that might otherwise be formed on the catheter's distal tip. As such, the slit 210 can be inserted through the skin and tissue of a patient without buckling, snagging, or shearing the skin or tissue. Furthermore, one or more slits 210 formed through the walls of a catheter can reduce the velocity of a fluid jet exiting the catheter tip, thus reducing the jet's impact and potential for damage to vein walls. Additionally, one or more slits 210 can reduce pressure loss and reduce the overall system pressure while permit higher injection rates for pressure-limited power injector systems.

The present invention may be embodied in other specific forms without departing from its structures, methods, or other essential characteristics as broadly described herein and claimed hereinafter. The described embodiments are to be considered in all respects only as illustrative, and not restrictive. The scope of the invention is, therefore, indicated by the appended claims, rather than by the foregoing description. All changes that come within the meaning and range of equivalency of the claims are to be embraced within their scope.

What is claimed is:

1. A catheter, comprising:
    a flexible catheter body having a lumen and a distal lumen opening, the lumen extending through the catheter body along a longitudinal axis of the catheter body; and
    a plurality of spiral slits formed through a wall of the catheter body, wherein the plurality of spiral slits are at least partially disposed on a tapered tip of the distal end of the catheter body, and wherein at least one of the spiral slits extends more than 180° around the catheter body at an angle of inclination between 15° and 75° from a longitudinal axis of the catheter body, each of the spiral slits forming two opposing slit surfaces that are substantially in contact when the catheter body is not used to inject a fluid, but that spread apart when the catheter body is used to inject a fluid thereby opening a fluid pathway between the opposing slit surfaces.

2. The catheter of claim 1, wherein at least one of the spiral slit extends proximally from a distal end of the catheter body less than or equal to one-quarter inch.

3. The catheter of claim 1, wherein at least one of the plurality of spiral slits extends between 3° to 720° around the catheter body.

4. The catheter of claim 1, wherein the angle of inclination is between 30° and 60°.

5. The catheter of claim 1, wherein at least one of the spiral slits is substantially disposed on a tapered tip of the distal end of the catheter body.

6. The catheter of claim 1, wherein the catheter body is tapered along substantially its entire length.

7. The catheter of claim 1, wherein the catheter is a peripheral catheter having a truncated length sufficient to access a peripheral vein of a patient.

8. The catheter of claim 5, wherein the catheter body is sized to be a fourteen gauge or smaller sized catheter.

9. The catheter of claim 1, wherein at least one of the spiral slits extends at least 360° around the catheter body.

10. The catheter of claim 1, wherein at least one of the spiral slits extends at least 540° around the catheter body.

11. A catheter, comprising:
    a flexible catheter body having a lumen and a distal lumen opening, the lumen extending through the catheter body along a longitudinal axis of the catheter body; and
    a plurality of spiral slits formed through a distal tapered portion of the catheter body, wherein the plurality of spiral slits are at least partially disposed on the distal tapered portion of the catheter body, and wherein at least one of the spiral slits extends more than 270° around the catheter body at an angle of inclination between 15° and 75° from a longitudinal axis of the catheter body, each of the spiral slits forming two opposing slit surfaces that are substantially in contact when the catheter body is not used to inject a fluid, but that spread apart when the catheter body is used to inject a fluid thereby opening a fluid pathway between the opposing slit surfaces.

12. The catheter of claim 11, wherein at least one of the spiral slits extends proximally from a distal end of the catheter body less than or equal to one-quarter inch.

13. The catheter of claim 11, wherein the angle of inclination is between 30° and 60°.

14. A peripheral catheter, comprising:
a catheter body having a lumen and a distal lumen opening, the lumen extending through the catheter body along a longitudinal axis of the catheter body; and
a plurality of spiral slits formed through a distal, tapered portion of the catheter body, the spiral slits extending proximally from a distal end of the catheter body at an angle of inclination between 15° and 75° from a longitudinal axis of the catheter body, wherein at least one of the spiral slits extends more than 360° around the catheter body, and wherein the at least one spiral slit forms two opposing slit surfaces, wherein the two opposing slit surfaces are substantially in contact along the length of the spiral slit when the catheter body is unused, but spread apart when the catheter body is used to inject a fluid thereby opening a fluid pathway between the opposing slit surfaces.

15. The peripheral catheter of claim 14, wherein at least one of the spiral slits extends at least 720° around the catheter body.

16. The peripheral catheter of claim 14, wherein the angle of inclination is between 30° and 60°.

17. The peripheral catheter of claim 14, wherein the spiral slits extend entirely on the distal, tapered portion.

18. The peripheral catheter of claim 14, wherein at least one of the spiral slits extends between 3° and 720° around the catheter body.

19. The peripheral catheter of claim 14, wherein the catheter body is tapered along substantially its entire length.

20. The peripheral catheter of claim 14, wherein the catheter body is sized to be a fourteen gauge or smaller sized catheter.

* * * * *